United States Patent
McGuigan et al.

(10) Patent No.: US 6,573,247 B1
(45) Date of Patent: Jun. 3, 2003

(54) ANTI-VIRAL PYRIMIDINE NUCLEOSIDE ANALOGUES

(75) Inventors: Christopher McGuigan, Whitchurch (GB); Christopher Yarnold, Didcot (GB); Garry Jones, Orrell Park (GB); Jan Balzarini, Heverlee (BE); Erik De Clercq, Lovenjoel (BE)

(73) Assignees: University College Cardiff Consultants Limited (GB); Rega Foundation (BE)

( * ) Notice: Subject to any disclaimer, the term of this patent is extended or adjusted under 35 U.S.C. 154(b) by 0 days.

(21) Appl. No.: 09/403,853

(22) PCT Filed: Apr. 27, 1998

(86) PCT No.: PCT/GB98/01222

§ 371 (c)(1),
(2), (4) Date: Jan. 6, 2000

(87) PCT Pub. No.: WO98/49177

PCT Pub. Date: Nov. 5, 1998

(30) Foreign Application Priority Data

Apr. 28, 1997 (GB) ............................................. 9708611

(51) Int. Cl.⁷ ........................ A61K 31/70; C07H 19/14; C07H 19/04
(52) U.S. Cl. ................... 514/43; 536/27.11; 536/27.13; 536/27.14
(58) Field of Search .......................... 536/27.11, 27.13, 536/27.14; 514/43

(56) References Cited

FOREIGN PATENT DOCUMENTS

| EP | 0 576 230 A | 12/1993 |
|---|---|---|
| JP | 62-255499 | 11/1987 |
| WO | WO 96/29336 | 9/1996 |
| WO | WO98/49177 A1 * | 11/1998 |
| WO | WO99/06422 A2 * | 2/1999 |
| WO | WO01/07087 A2 * | 2/2001 |
| WO | WO01/07088 A2 * | 2/2001 |
| WO | WO01/07454 A1 * | 2/2001 |

OTHER PUBLICATIONS

Tolstikov et al.(I), "Novel Type of Interaction of 5–Iodopyrimidinonucleosides with Alkynes," *Izv. Akad. Nauk, Ser. Khim.*, (Issue No. 6), 1449–1450 (1992); *Chemical Abstracts*, 118(13), p. 855, Abstract No. 124938m (Mar. 29, 1992); only Abstract supplied.*

Tolstikov et al.(II), "New Type of Reaction of 5–Iodopyrimidine Nucleosides with Alkynes," *Izv. Akad. Nauk, Ser. Khim.*, (Issue No. 3), 596–598 (1993); *Chemical Abstracts*, 124(7), p. 1379, Abstract No. 87652q (Feb. 12, 1996); only Abstract supplied.*

Morvan et al., "α–Oligodeoxynucleotides Containing 5–Propynyl Analogues of α–Deoxyuridine and α–Deoxycytidine: Synthesis and Base Pairing Properties," *Tetrahedron*, 54(1/2), 71–82 (Jan. 1, 1998).*

(List continued on next page.)

*Primary Examiner*—James O. Wilson
*Assistant Examiner*—Lawrence E Crane
(74) *Attorney, Agent, or Firm*—Woodcock Washburn LLP

(57) ABSTRACT

A compound having formula (I), wherein R is selected from the group comprising $C_5$ to $C_{20}$ alkyl, $C_5$ to $C_{20}$ cycloalkyl, halogens, aryl and alkylaryl; R' is selected from the group comprising hydrogen, alkyl, cycloalkyl, halogens, amino, alkylamino, dialkylamino, nitro, cyano, alkyoxy, aryloxy, thiol, alkylthiol, arythiol, alkyl; R" is selected from the group comprising hydrogen, alkyl, cycloalkyl, halogens, alkyloxy, aryloxy and aryl; Q is selected from the group comprising O, S and $CY_2$, where Y may be the same or different and is selected from H, alkyl and halogens; X is selected from the group comprising O, NH, S, N-alkyl, $(CH_2)_n$ where n is 1 to 10, and $CY_2$ where Y may be the same or different and is selected from hydrogen, alkyl and halogens; Z is selected from the group comprising O, S, NH, and N alkyl; U" is H and U' is selected from H and $CH_2T$, or U' and U" are joined so as to form a ring moiety including Q wherein U'–U" together is respectively selected from the group comprising —CTH—CT'T"— and —CT=CT— and —CT"=CT'—, so as to provide ring moieties selected from the group comprising formula (II) and (III) wherein T is selected from the group comprising OH, H, halogens, O-alkyl, O-acyl, O-aryl, CN, $NH_2$ and $N_3$; T' is selected from the group comprising H and halogens and where more than one T' is present they may be the same or different; T" is selected from the group comprising H and halogens, and W is selected from the group comprising H, a phosphate group and a pharmacologically acceptable salt, derivative or prodrug thereof shows potent anti-viral activity against, for example, varicella zoster virus and cytomegalovirus.

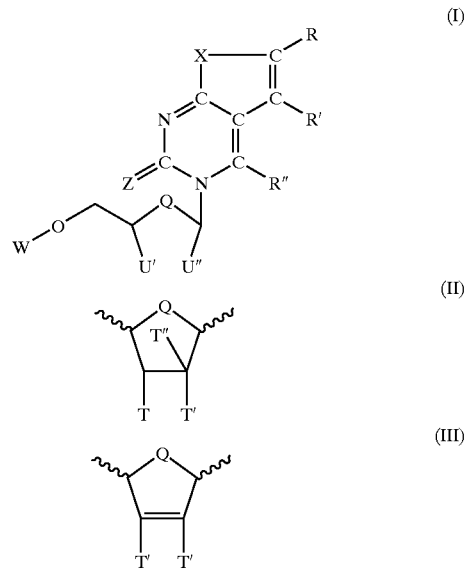

14 Claims, No Drawings

OTHER PUBLICATIONS

Inoue et al., "Synthesis of Dodecadeoxynucleotides Containing a Pyrrolo[2,3-d]-pyrimidine Nucleoside and Their Base-pairing Ability," *Nippon Kagaku Kaishi* (J. Chem. Soc. Japan, Chemistry and Industrial Chemistry), (Issue No. 7), 1214–1220 (Jul., 1987); *Chemical Abstracts*, 108, Abstract No. 187183a (May 23, 1988). Copy of abstract supplied by applicant.*

Crisp, G.T. et al., "Palladium-catalyzed coupling of terminal alkynes with 5-(trifluoromethanesulfonyloxy)pyrimidine nucleosides," *J. Org. Chem.*, 1993, 58, 6614–6619 (Issue No. 24).

Cruickshank, K.A. et al., "Oligonucleotide Labelling: A Concise Synthesis of a Modified Thymidine Phosphoramidite," *Tetra.Lett.*, 1988, 29(41), 5221–5224.

De Clercq, E. et al., "Nucleic acid related compounds. 40. Synthesis and biological activities of 5-alkynyluracil nucleosides," *J. Med. Chem.*, 1983, 26(5), 661–666.

Kumar, R. et al., "Synthesis and Properties of 5-(1, 2-Dihaloethyl)-2'-deoxyuridines and Related Analogues," *J. Heterocyclic Chem.*, 1991, 28, 1917–1925 (Dec., 1991).

Kumar, R. et al., "Synthesis of 5-(1-azidovinyl) and 5-[2-(1-azirinyl)] analogs of 2'-deoxyuridine," *Can. J. Chem.*, 1996, 74, 1609–1615.

Robins, M.J. et al., "Nucleic acid related compounds. 39. Efficient conversion of 5-iodo to 5-alkynyl and derived 5-substituted uracil bases and nucleosides," *J. Org. Chem.*, 1983, 48, 1854–1862 (Issue No. 11).

Robins, M.J. et al., "Nucleic Acid Related Compounds. 31. Smooth and Efficient Palladium-Copper Catalyzed Coupling of Terminal Alkynes with 5-Iodouracil Nucleosides," *Tetra. Lett.* 1981, 22, 421–424.

Woo, J. et al., "G/C-modified oligodeoxynucleotides with selective complementarity: synthesis and hybridization properties," *Nucl. Acids Res.*, 1996, 24(13), 2470–2475.

* cited by examiner

ANTI-VIRAL PYRIMIDINE NUCLEOSIDE ANALOGUES

This application is a national stage application filed under 35 U.S.C. §371 of PCT International Application No. PCT/GB98/01222 filed on Apr. 27, 1998.

The present invention relates to a new class of nucleoside analogues and to their therapeutic use in the prophylaxis and treatment of viral infection for example by varicella zoster virus (VZV). Varicella zoster virus is the aetiological agent in chickenpox and shingles which can cause considerable human illness and suffering.

There has been considerable interest in the development of 5-substituted pyrimidine deoxynucleosides as putative antiviral agents.

Tetrahedron Letters, 22, 421, 1981, M. J. Robins and P. J. Barr describes a method of coupling terminal alkynes with protected 5-iodouracil nucleotides in the presence of a catalyst to give the corresponding 5-(alkyn-1-yl) uracil nucleosides.

J. Med. Chem. 26, 661, 1983, E. de Clercq, J. Descamps, J. Balzarini, J. Giziewicz, P. J. Barr and M. J. Robins describes a catalytic process for coupling terminal alkynes with 5-iodo-1-(2,3,5,-tri-O-p-toluyl-β-D-arabinofuranosyl) uracil and 5-iodo-3',5'-di-O-p-toluyl-2'-deoxyuridine. A cyclized by-product having methyl substituted at the 6-position was isolated and characterised spectroscopically.

J. Org. Chem. 48, 1854, 1983, M. J. Robins and P. J. Barr describes catalytic coupling of terminal alkynes with 5-iodo-1-methyluracil and 5-iodouracil nucleotides protected as their p-toluyl esters. The article also describes the conversion of 5-hexynyl-2'-deoxyuridine to cyclized 6-n-butyl-3-(2-deoxy-β-D-erythro-pentofuraosyl)furano[2,3-d]pyrimidin-2-one.

Tetrahedron Letters 29, 5221, 1988, K. A. Cruickshank and D. L. Stockwell describes the catalytic condensation of 5'-dimethoxytrityl-5-iodo-2'-deoxyuridine with N-trifluoroacetyproparglyamine and subsequent conversion to the 3'-phosphoramidite.

J. Heterocyclic Chem. 28, 1917, 1991, R. Kumar, E. E. Knaus and L. I. Wiebe describes a reaction employing 5-(1-fluoro-2-bromoethyl)-3',5'-di-O-acetyl-2'-deoxyuridine and producing a compound having the formula:

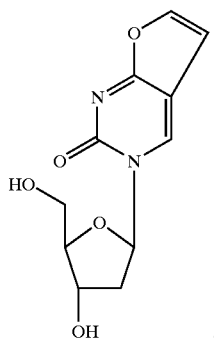

J. Org. Chem. 1993, 58, 6614, G. T. Crisp and B. L. Flynn describes palladium catalysed couplings of terminal alkynes with a variety of oxyuridines. One coupling described is that between 5-ethynyl-2'-deoxyuridine and a range of fluorinated aryl compounds.

Nucleic Acids Research 1996, 24, 2470, J. Woo, R. B. Meyer and H. B. Gamper describes a process for the preparation of 3-(2'-deoxy-β-D-ribofuranosyl)-pyrrolo-[2,3-d]-pyrimidine-2(3H)-one.

Can. J. Chem. 74, 1609, 1996, R. Kumar, L. I. Wiebe, E. E. Knaus describes a range of deoxyuridine compounds and their various anti-viral activity. A compound of the formula:

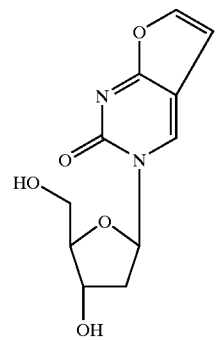

was found to be inactive in the vitro assays against HSV-1, HSV-2, VZV and CMV.

JP 62255499 (Teijin Ltd) describes the preparation of fluorescent nucleosides or nucleotides and their use for DNA hybridization probes. The compounds described have the general formula:

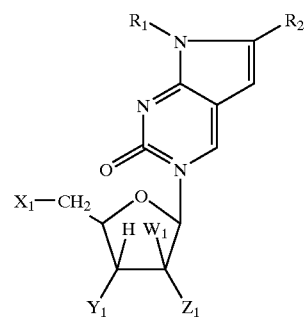

wherein $X_1$ and $Y_1$ are $HO[P(O)(OH)O]n$, $Z_1$ is H or $HO[P(O)(OH)O]m$, with m and n=0 to 3, W1 is H or HO and $R_1$ and $R_2$ are H or $C_1$ to $C_{10}$ alkyl.

Nippon Kagaku Kaishi 7, 1214, 1987 describes the synthesis of fluorescent dodecadeoxy ribonucleotides having the general formula:

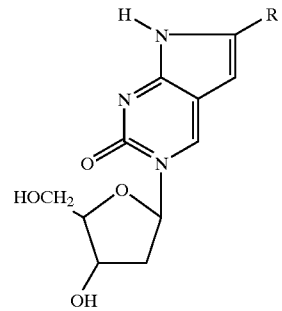

where R can be H or butyl.

It is an object of the present invention to provide a novel class of nucleoside analogues.

It is a further object of the present invention to provide a novel class of nucleoside analogues for therapeutic use in the prophylaxis and treatment of viral infection for example by varicella zoster virus.

According to a first aspect of the present invention there is provided a compound having formula I as follows:

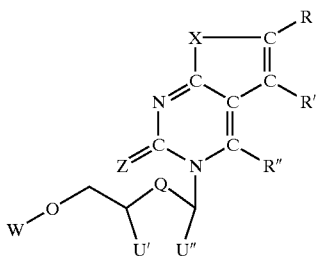

wherein
- R is selected from the group comprising $C_5$ to $C_{20}$ alkyl, $C_5$ to $C_{20}$ cycloalkyl, halogens, aryl and alkylaryl;
- R' is selected from the group comprising hydrogen, alkyl, cycloalkyl, halogens, amino, alkylamino, dialkylamino, nitro, cyano, alkyoxy, aryloxy, thiol, alkylthiol, arylthiol, and aryl;
- R" is selected from the group comprising hydrogen, alkyl, cycloalkyl, halogens, alkyloxy, aryloxy and aryl;
- Q is selected from the group comprising O, S and $CY_2$, where Y may be the same or different and is selected from H, alkyl and halogens;
- X is selected from the group comprising O, NH, S, N-alkyl, $(CH_2)_n$ where n is 1 to 10, and $CY_2$ where Y may be the same or different and is selected from hydrogen, alkyl and halogens;
- Z is selected from the group comprising O, S, NH and N-alkyl;
- U" is H and U' is selected from H and $CH_2T$, or U' and U" are joined so as to provide a ring moiety including Q wherein
- U'–U" together is respectively selected from the group comprising —CTH—CT'T"— and —CT'=CT'—, so as to provide ring moieties selected from the group comprising

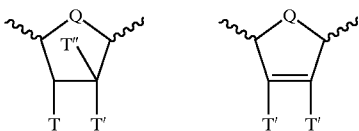

wherein
- T is selected from the group comprising OH, H, halogens, O-alkyl, O-acyl, O-aryl, CN, $NH_2$ and $N_3$;
- T' is selected from the group comprising H and halogens and where more than one T' is present they may be the same or different;
- T" is selected from the group comprising H and halogens; and
- W is selected from the group comprising H, a phosphate group and a phosphonate group.

It is to be understood that the present invention extends to compounds according to formula I wherein the group W is modified to any pharmacologically acceptable salt or derivative of —H, phosphates or phosphonates. The present invention also includes any compound which is a pro-drug of the compound according to formula I, any such pro-drug being provided by modification of the moiety W, wherein W is selected from phosphates and derivatives thereof, and phosphonates and derivatives thereof.

Each of R, R' and R" may be substituted or unsubstituted and may be branched or unbranched. When any of R, R' and R" are alkyl or cycloalkyl they may be saturated or unsaturated. The nature, position and number of any substituents and unsaturation present may be varied. R may contain aryl or heteroaryl groups which may vary in nature, position or number. A preferred position is the terminus position in R. Examples of suitable substituents include OH, halogens, amino, CN, CHOH, $CO_2$alkyl, $CONH_2$, CONHalkyl, SH, S-alkyl and $NO_2$, wherein alkyl is suitably $C_1$ to $C_5$. Suitably any substituent in R when R is alkyl or cycloalkyl is non-polar, more suitably any such substituent is additionally hydrophobic.

Preferably R is an alkyl group. More preferably R is a $C_7$ to $C_{20}$ alkyl group, which may optionally carry substituents such as halogens. Even more preferably R is a $C_8$ to $C_{14}$ group, particularly preferred is R being straight chain $C_{10}H_{21}$.

When R is aryl or alkylaryl it can be substituted. Alkylaryl can be aryl with one or more $C_1$ to $C_{10}$ groups attached which themselves can be substituted or unsubstituted. Aryl groups can include benzyl groups and heterosubstituted 5, 6 or 7 numbered rings. Either an aryl or an alkyl portion of an alkylaryl group can be attached to the ring structure. If desired R can, optionally substituted as above, for example be —$(CH_2)_n$-aryl-$(CH_2)_m$H, where n and m are each more than 1 and n+m≦10 and the aryl is preferably $C_6H_4$. R cannot be any radical equivalent to 4-$FC_6H_5$, $C_6F_5$, 4-$MeOC_6H_5$, 3,5-$(CF_3)_2C_6H_4$, 3,5-$F_2C_6H_4$, 4-$CF_3C_6H_5$ or $C_6H_5$.

Suitably R' is selected from the group comprising $C_1$ to $C_{10}$ alkyl, $C_3$ to $C_{10}$ cycloalkyl, $C_1$ to $C_{10}$ alkylamino, $C_1$ to $C_{10}$ dialkylamino, $C_1$ to $C_{10}$ alkyloxy, $C_6$ to $C_{10}$ aryloxy, $C_1$ to $C_{10}$ alkylthiol, $C_6$ to $C_{10}$ arylthiol and $C_6$ to $C_{10}$ aryl. Suitably R" is selected from the group comprising $C_1$ to $C_{10}$ alkyl, $C_3$ to $C_{10}$ cycloakyl, $C_1$ to $C_{10}$ alkyloxy, $C_6$ to $C_{10}$ aryloxy and $C_6$ to $C_{10}$ aryl.

Preferably each of R' and R" is a small alkyl i.e. a $C_1$ to $C_2$ alkyl group or H. More preferably each of R' and R" is H.

Throughout the present specification "halogen" is taken to include any of F, Cl, Br and I.

Preferably Q is $CH_2$, S or O. More preferably Q is O. Where Q is $CY_2$ and includes a halogen, the halogen is preferably fluorine. Y is preferably H.

Preferably X is O, S or NH. More preferably X is O. Where X is $(CH_2)_n$, n is preferably 1 or 2, most preferably 1. X cannot be NH or N-alkyl when R is an unsubstituted $C_5$ to $C_{10}$ alkyl group, unless Q is other than O. Suitably when X is N-alkyl, alkyl is $C_1$ to $C_5$ alkyl and when X is $CY_2$ at least one Y is $C_1$ to $C_5$ alkyl.

Preferably Z is O. Where Z is N-alkyl, suitably the alkyl is $C_1$ to $C_5$ alkyl.

Preferably U' and U" are joined to provide the saturated ring moiety including T, T' and T". Preferably T, T' and T" in such a ring moiety are respectively OH, H and H.

Preferably T is OH. When T is a halogen it is preferably F.

Preferably each of T' and T" is H. When either or both of T' and T" is halogen it is preferably fluorine.

When W is a moiety which renders the compound a pro-drug of the compound according to formula I it is to be understood that the term pro-drug includes the corresponding free base of each of the nucleosides described. The free base may moreover have direct antiviral action not dependent on metabolism to the corresponding nucleoside analogue.

It is also to be understood that "phosphate" includes diphosphates and triphosphates and "phosphonate" includes diphosphonates and triphosphonates. Hence W includes pharmacologically acceptable salts and derivatives of phosphates, diphosphates and triphosphates and of phosphonates, diphosphonates and triphosphonates. It also includes any moiety which provides a compound which is a pro-drug of the compound according to formula I, wherein W is selected from phosphates, diphosphates and triphosphates and derivatives thereof, and phosphonates, diphosphonates and triphosphonates and derivatives thereof.

Each compound may be the pure stereoisomer coupled at each of its chiral centres or it may be inverted at one or more of its chiral centres. It may be a single stereoisomer or a mixture of two or more stereoisomers. If it is a mixture the ratio may or may not be equimolar. Preferably the compound is a single stereoisomer. The compound may be in either enantiomeric form i.e. it may be either the D or L enantiomer either as a single stereoisomer or as a mixture of the two enantiomers. More preferably the compound has a stereochemistry resembling natural deoxy nucleosides derived from β-D-2-deoxyribose. However other enantiomers particularly the L enantiomers may be employed.

It is to be understood that the present invention extends to compounds wherein the sugar moiety and phosphate if present have either together or separately been modified as well known to a person skilled in art.

It is also possible for a compound embodying the present invention to be in a sugar form as for example modified and derived from a D-xylo sugar system.

Particularly preferred compounds embodying the present invention have the following formulas:

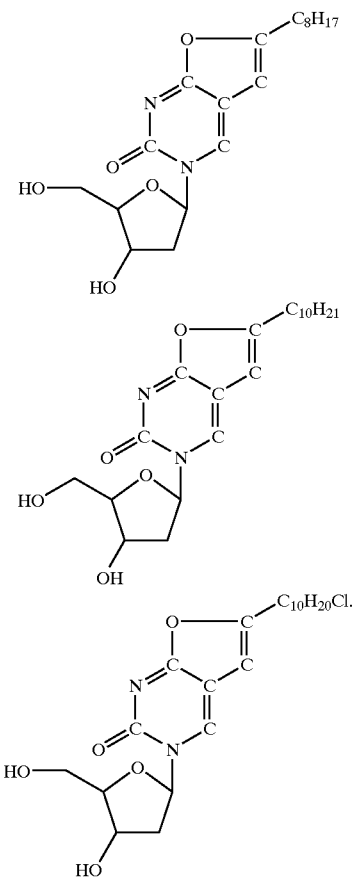

According to a further aspect of the present invention there is provided a method for preparing compounds having Formula I above wherein a 5-halo nucleoside analogue is contacted with a terminal alkyne in the presence of a catalyst. Alternatively 5-alkynyl nucleoside can be cyclised in the presence of a catalyst. Suitably the catalyst is a copper catalyst. The 5-alkynyl nucleoside has the general formula:

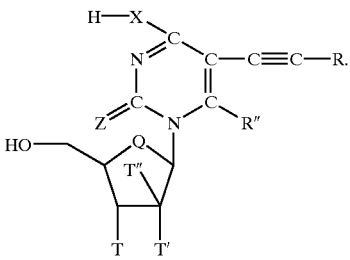

Compounds embodying the present invention can show anti-viral activity. In particular it has surprisingly been found that compounds embodying the present invention can show antiviral activity against for example varicella zoster virus and/or cytomegalovirus.

According to a further aspect of the present invention there is provided a compound according to the present invention for use in a method of treatment, suitably in the prophylaxis or treatment of a viral infection. In this aspect of the present invention when X is NH or N-alkyl R can be $C_7$ to $C_{20}$ alkyl.

According to a further aspect of the present invention there is provided use of a compound according to the present invention in the manufacture of a medicament for the prophylaxis or treatment of viral infection. In this aspect of the present invention when X is NH or N alkyl R can be $C_7$ to $C_{20}$ alkyl.

According to a further aspect of the present invention there is provided a method of prophylaxis or treatment of viral infection comprising administration to a patient in need of such treatment an effective dose of a compound according to the present invention. In this aspect of the present invention when X is NH or N alkyl R can be $C_7$ to $C_{20}$ alkyl.

According to a further aspect of the present invention there is provided use of a compound of the present invention in the manufacture of a medicament for use in the prophylaxis or treatment of a viral infection, particularly an infection with the varicella zoster virus or an infection with cytomegalovirus. In this aspect of the present invention when X is NH or N alkyl R can be $C_7$ to $C_{20}$ alkyl. When the infection is the varicella zoster virus or cytomegalovirus then also in this aspect of the invention R can be aryl or alkylaryl, without the exclusion of R not being a radical equivalent to $4\text{-}FC_6H_5$, $C_6H_5$, $4\text{-}MeOC_6H_5$, $3,5(CF_3)_2C_6H_4$, $3,5,\text{-}F_2C_6H_4$, $4\text{-}CF_3C_6H_5$ or $C_6H_5$.

According to a further aspect of the present invention there is provided a pharmaceutical composition comprising a compound of the present invention in combination with a pharmaceutically acceptable excipient. In this aspect of the invention when X is NH or N alkyl R can be $C_7$ to $C_{20}$ alkyl.

According to a further aspect of the present invention there is provided a method of preparing a pharmaceutical composition comprising the step of combining a compound of the present invention with a pharmaceutically acceptable excipient. In this aspect of the invention when X is NH or N alkyl R can be $C_7$ to $C_{20}$ alkyl.

The medicaments employed in the present invention can by administered by oral or parenteral routes, including intravenous, intramuscular, intraperitoneal, subcutaneous, transdermal, airway (aerosol), rectal, vaginal and topical (including buccal and sublingual) administration.

For oral administration, the compounds of the invention will generally be provided in the form of tablets or capsules, as a powder or granules, or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The compounds of the invention may also be presented as liposome formulations.

In general a suitable dose will be in the range of 0.1 to 300 mg per kilogram body weight of the recipient per day, preferably in the range of 1 to 25 mg per kilogram body weight per day and most preferably in the range 5 to 10 mg per kilogram body weight per day. The desired dose is preferably presented as two, three, four, five or six or more sub-doses administered at appropriate intervals throughout the day. These sub-doses may be administered in unit dosage forms, for example, containing 10 to 1500 mg, preferably 20 to 1000 mg, and most preferably 50 to 700 mg of active ingredient per unit dosage form.

Embodiments of the present invention will now be described by way of example only. It will be appreciated that modifications to detail may be made whilst still falling within the scope of the invention.

Experimental

In the following examples the bicyclic rings of the compounds are numbered following recommended IUPAC guidelines. Thus 3-(2'-Deoxy-β-D-ribofuranosyl)-6-octyl-2,3-dihydrofuro[2,3-d]pyrimidin-2-one has the structure and is numbered as follows:

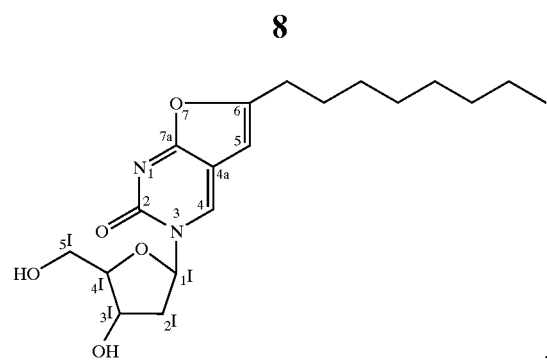

Preparation of 5-(1-Decynyl)-2'-deoxyuridine

To a stirred solution of 5-iodo-2'-deoxyuridine (800 mg, 2.26 mmol) in dry dimethylformaldehyde (8 ml), at room temperature under a nitrogen atmosphere, was added dry diisopropylethylamine (584 mg, 0.80 ml, 4.52 mmol), 1-decyne (937 mg, 1.22 ml, 6.78 mmol), tetrakis (triphenylphosphine) palladium (0) (261 mg, 0.226 mmol) and copper (I) iodide (86 mg, 0.452 mmol). The reaction mixture was stirred at room temperature for 19 hours, after which time the reaction mixture was concentrated in vacuo. The resulting residue was dissolved in dichloromethane/methanol (1:1) (6 ml) and an excess of Amberlite IRA-400 ($HCO_3^-$ form) was added and the mixture was stirred for 30 minutes. The resin was then filtered, washed with methanol and the combined filtrate was evaporated to dryness. The crude product was purified by silica gel column chromatography using an initial eluent of ethyl acetate, then changing to ethyl acetate/methanol (9:1) via a gradient. The appropriate fractions were combined and the solvent removed in vacuo to yield the product as a cream solid (490 mg, 60%). Recrystallization of the product from hot dichloromethane yielded the pure product as fine white crystals (376 mg, 46%).

$^1$H-nmr (d$_6$-DMSO;300 MHz): 11.56(1H, br.s, NH-3), 8.11(1H, s, H-6), 6.12(1H, dd, $^3$J=6.6 Hz, H-1'), 5.25(1H, d, $^3$J=4.2 Hz, 3'-OH), 5.09(1H, t, 5'-OH), 4.24(1H, m, H-3'), 3.79(1H, m, H-4'), 3.59(2H, m, H-5'), 2.36(2H, t, $^3$J=6.8 Hz, α-CH$_2$), 2.12(2H, m, H-2'$_a$ and H-2'$_b$), 1.47(2H, m, β-CH$_2$), 1.38–1.26(10H, m, 5×CH$_2$), 0.87 (3H, t, CH$_3$). $^{13}$C-nmr (d$_6$-DMSO; 75 MHz): 16.2(CH$_3$), 21.0, 24.3, 30.4, 30.5, 30.8, 30.9(6×CH$_2$), 33.5(α-CH$_2$), 41.7(C-2'), 63.2(C-5'), 72.4(C-3'), 75.1, 86.8, 89.8, 95.5(C-4', C-β, C-1', C-α), 101,3(C-5), 144.9(C-6), 151.7(C-2), 164.0(C-4). Mass spectrum (ES−MS(+ve)): 387[M+Na]$^+$, 365[M+H]$^+$.

All $^1$H and $^{13}$C-NMR spectra were recorded on a Bruker Avance DPX300 spectrometer at 300 MHz and 75 MHz respectively. Chemical shifts were recorded in parts per million (ppm) downfield from tetramethylsilane.

Low resolution mass spectra were recorded on a Fisons Instruments VG Platform Electrospray mass spectrometer run in either positive or negative ion mode, with acetronitrile/water as the mobile phase.

EXAMPLES 1 TO 6

Examples 1 to 6 each embody the present invention and illustrate the effect of chain length in the alkyl group R. In terms of Formula I above each compound had the following components X=O, Z=O Q=O, W=H, R"=R'=H, T=OH and T'=T"=H.

EXAMPLE 1

3-(2'-Deoxy-β-D-ribofuranosyl)-6-dodecyl-2,3dihydrofuro[2,3-d]pyrimidin-2-one

To a stirred solution of 5-(1-tetradecynyl)-2'-deoxyuridine (382 mg, 0.91 mmol) in methanol/triethylamine (7:3) (30 ml), at room temperature under a nitrogen atmosphere, was added copper (I) iodide (45 mg, 0.225 mmol). The reaction mixture was then heated to reflux and stirred for 5 hours. The solvent was removed in vacuo and the crude product purified by silica gel column chromatography, using an initial eluent of dichloromethane/methanol (9:1), followed by an eluent of dichloromethane/methanol (8:2). The appropriate fractions were combined and the solvent removed in vacuo, yielding the pure product as a white solid. (188 mg, 49%).

$^1$H-nmr (d$_6$-DMSO; 300 MHz): 8.70 (1H, s, H-4), 6.27 (1H, s, H-5), 6.18 (1H,dd, $^3$J=5.7 Hz, 6.0 Hz, H-1'), 5.19(1H, d, $^3$J=4.2 Hz, 3'-OH), 5.05 (1H, t, $^3$J=4.9 Hz, 5'-OH), 4.25 (1H, m, H-3'), 3.91 (1H, m, H-4'), 3.66 (2H, m, H-5'), 2.60 (2H, t α-CH$_2$), 2.42 and 2.03 (2H, m, H-2'$_a$ and H-2'$_b$), 1.61 (2H, m, β-CH$_2$), 1.21 (18H, br.m, 9×CH$_2$), 0.83 (3H, m, CH$_3$). $^{13}$C-nmr (d$_6$-DMSO; 75 MHz): 14.7 (CH$_3$), 23.0, 27.2, 28.4, 29.3, 2×29.6, 2×29.8, 2×29.9 (10×CH$_2$), 32.2 (α-CH$_2$), 42.3(C-2'), 61.5 (C-5'), 70.3 (C-3'), 88.2, 88.9 (C-1' and C-4'), 100.2 (C-5), 107.6 (C-4a), 137.3 (C-4), 154.8 (C-2), 159.1 (C-6), 172.0 (C-7a). Mass spectrum (ES–MS (+ve)); m/z 484 (15%, [M+Cu]$^+$), 459 (20%, [M+K]$^+$), 443 (40%, [M+Na]$^+$), 421 (40%, [M+H]$^+$, 305 (100%, [base+H]$^+$). Elemental analysis (found: C, 65.62%; H, 8.82%; N, 6.90%. C$_{23}$H$_{36}$N$_2$O$_5$ requires: C, 65.69%; H, 8.63%; N, 6.66%).

EXAMPLE 2

3-(2'-Deoxy-β-D-ribofuranosyl)-6-decyl-2,3-dihydrofuro[2,3-d]pyrimidin-2-one

To a solution of 5-(1-dodecynyl)-2'-deoxyuridine (130 mg, 0.33 mmol) in 10 ml of triethylamine/methanol (7:3) was added copper (I) iodide (8 mg) and the solution heated to reflux for 3 hours. Volatile materials were evaporated and the residue was taken up in 20 ml of chloroform and washed with 2% aqueous solution of disodium ethylene diamine tetra acetate (2×10 ml) and water (10 ml). The combined aqueous layers were extracted with chloroform (2×250 ml). The combined organic layers were dried (MgSO$_4$) and the solvent removed in vacuo to give a solid (59 mg, 45%) which was recrystallized from ethanol and diisopropyl ether (27 mg, 21%).

m.p. 164–165° C. R$_f$ 0.05(EtOAc). $^1$H-nmr (d$_6$-DMSO; 300 MHz): 8.67(1H, s, H-4), 6.43(1H, s, H-5), 6.16(1H, t, $^3$J=6.1 Hz, H-1'), 5.28(1H, d, $^3$J=4.2 Hz, 3'-OH), 5.12(1H, t, $^3$J=5.1 Hz, 5'-OH), 4.22(1H, m, H-3'), 3.89(1H, m, H-4'), 3.63(2H, m, H-5'), 2.64(2H, t, $^3$J=7.2 Hz, α-CH$_2$), 2.33 and 2.04(2H, m, H-2'$_a$ and H-2'$_b$), 1.60(2H, m, β-CH$_2$), 1.28–1.23(14H, m, 7×CH$_2$), 0.85, (3H, t, J=6.9 Hz, CH$_3$). $^{13}$C-nmr(d$_6$-DMSO; 75 MHz): 14.2(CH$_3$), 22.3, 26.6, 27.6, 28.6, 28.9, 28.9, 29.1, 29.2, 31.5 (9×CH$_2$), 41.4(C-2'), 61.0(C-5'), 69.7(C-3'), 87.6, 88.3 (C-1', C-4'), 106.6, 100.0 (C-4a, C-5), 137.0 (C-4), 154.0 (C-6), 158.5 (C-2), 171.4 (C-7a). Mass spectrum (ES-MS(+ve)): 415[M+Na]$^+$.

EXAMPLE 3

3-(2'-Deoxy-β-D-ribofuranosyl)-6-octyl-2,3-dihydrofuro[2,3-d]pyrimidin-2-one

To a stirred solution of 5-(1-decynyl)-2'-deoxyuridine (216 mg, 0.59 mmol) in methanol/triethylamine (7:3) (20 ml), at room temperature under a nitrogen atmosphere, was added copper (I) iodide (20 mg, 0.10 mmol). The reaction mixture was then heated to reflux and stirred for 5 hours. The solvent was removed in vacuo and the crude product purified by silica gel column chromatography, using an initial eluent of dichloromethane/methanol (9:1), followed by an eluent of dichloromethane/methanol (8:2). The appropriate fractions were combined and the solvent removed in vacuo, yielding an orange/brown solid. The crude product was triturated and washed with acetone, followed by drying, yielding the pure product as a fine white powder (118 mg, 55%).

$^1$H-nmr(d$_6$-DMSO; 300MHz): 8.63(1H, s, H-4), 6.39(1H, s, H-5), 6.12(1H, dd, $^3$J=6.0 Hz, 6.4 Hz, H-1'), 5.25(1H, d, $^3$J=4.5 Hz, 3'-OH), 5.09(1H, t, 5'-OH), 4.19(1H, m, H-3'), 3.86(1H, m, H-4'), 3.60(2H, m, H-5'), 2.60(2H, t, $^3$J=7.2 Hz, α-CH$_2$), 2.33 and 2.00(2H, m, H-2'$_a$ and H-2'$_b$), 1.57(2H, m, β-CH$_2$), 1.21(10H, br.m, 5×CH$_2$), 0.81(3H, t, CH$_3$). $^{13}$C-nmr(d$_6$-DMSO; 75 MHz): 14.4(CH$_3$), 22.5, 26.8, 27.8, 28.8, 29.1 (5×CH$_2$), 31.7 (β-CH$_2$), 39.1 (α-CH$_2$), 41.6(C-2'), 61.2(C-5'), 70.1(C-3'), 87.8, 88.5(C-1' and C-4'), 100.2(C-5), 106.8(C-4a), 137.2(C-4), 154.2(C-2, 158.7(C-6), 171.6 (C-7a). Mass spectrum (ES–MS(+ve)): 387 [M+Na]$^+$, 365 [M+H]$^+$.

EXAMPLE 4

3-(2'-Deoxy-β-D-ribofuranosyl)-6-hexyl-2,3-dihydrofuro[2,3-d]pyrimidin-2-one

To a stirred solution of 5-iodo-2'-deoxyuridine (800 mg, 2.26 mmol) in dry dimethylformaldehyde (8 ml), at room temperature under a nitrogen atmosphere, was added dry diisopropylethylamine (584 mg, 0.80 ml, 4.52 mmol), 1-octyne (747 mg, 1.00 ml, 6.78 mmol), tetrakis (triphenylphosphine) palladium(0) (261 mg, 0.226 mmol) and copper (I) iodide (86 mg, 0.452 mmol). The reaction mixture was stirred at room temperature for 19 hours, after which time thin layer chromatography (ethyl acetate/methanol (95:5)) of the reaction mixture showed complete conversion of the starting material. Copper (I) iodide (80 mg, 0.40 mmol) and triethylamine (15 ml) were then added to the reaction mixture, which was subsequently heated at 70–80° C. for 4 hours. The reaction mixture was then concentrated in vacuo and the resulting residue was dissolved in dichloromethane/methanol (1:1) (8 ml) and an excess of Amberlite IRA-400 (HCO$_3$$^-$ form) was added and the mixture was stirred for 30 minutes. The resin was then filtered, washed with methanol and the combined filtrate was evaporated to dryness. The crude product was initially triturated with acetone and then purified by silica gel column chromatography using an initial eluent of dichloromethane/methanol (95:5), followed by an eluent of dichloromethane/methanol (9:1). The appropriate fractions were combined and the solvent removed in vacuo to yield the product as a cream solid (196 mg, 26%). Trituration of the product with petroleum ether yielded the pure product as a fine white solid (176 mg, 23%).

$^1$H-nmr(d$_6$-DMSO; 300 MHz): 8.64(1H, s, H-4), 6.40 (1H, s, H-5), 6.13(1H, dd, $^3$J=6.0 Hz, 6.4 Hz, H-1'), 5.25(1H, d, $^3$J=4.1 Hz, 3'-OH), 5.10(1H, t, 5'-OH), 4.19(1H, m, H-3'), 3.87(1H, m, H-4'), 3.60(2H, m, H-5'), 2.61(2H, t, $^3$J=7.2 Hz, α-CH$_2$), 2.33 and 2.01(2H, m, H-2'$_a$ and H-2'$_b$), 1.57(2H, m, β-CH$_2$), 1.25(6H, br.m, 3×CH$_2$), 0.82(3H, m, CH$_3$). $^{13}$C-nmr (d$_6$-DMSO; 75 MHz): 16.2(CH$_3$), 24.2, 28.6, 29.6 (3×CH$_2$), 30.3 (β-CH$_2$), 33.1(α-CH$_2$), 43.4(C-2'), 63.0(C-5'), 71.9(C-3'), 89.6, 90.3(C-1' and C-4'), 102.0(C-5), 108.6(C-4a), 139.0 (C-4), 156.0(C-2), 161.7(C-6), 173.4(C-7a). Mass spectrum (ES-MS(+ve)): 359[M+Na]$^+$, 337[M+H]$^+$.

Each of the products of Examples 1, 2, 3 and 4 was tested in vitro in tissue culture assays for potent antiviral action with respect to varicella zoster virus (VZV). Acyclovir was included in the test procedure as a control. The results are given in Table I below. VZV (strains OKa and YS) induced cytopathogenicity in human embryonic lung fibroblast (HEL) cells was measured 7 days post infection. $EC_{50}$ was defined as the drug concentration (in $\mu M$) required to reduce virus-induced cytopathicity by 50%.

TABLE I

| Compound  | $EC_{50}$/VZV/$\mu M$ | $CC_{50}$/$\mu M$ |
|-----------|------------------------|-------------------|
| Example 1 | ≦1.2                   | >200              |
| Example 2 | 0.005                  | >50               |
| Example 3 | 0.003                  | >50               |
| Example 4 | 1.3                    | >200              |
| Acyclovir | 0.2                    | >100              |

Thus in terms of general formula I where R is a straight chain alkyl group having 10 or 8 C atoms and X is O, i.e. equivalent to Examples 2 and 3 respectively, extremely potent antiviral activity was displayed with respect to varicella zoster virus. Where R is a straight chain alkyl group having 12 or 6 C atoms and X is O, i.e. equivalent to Examples 1 and 3 respectively, antiviral activity comparable to acyclovir was displayed.

EXAMPLE 5

3-(2'-Deoxy-β-D-ribofuranosyl)-6-pentyl-2,3-dihydrofuro[2,3-d]pyrimidin-2-one

To a stirred solution of 5-(1-heptynyl)-2'-deoxyuridine (125 mg, 0.39 mmol) in methanol/triethylamine (7:3) (14 ml), at room temperature under a nitrogen atmosphere, was added copper (I) iodide (15 mg, 0.075 mmol). The reaction mixture was then heated to reflux and stirred for 8 hours. The solvent was removed in vacuo and the crude product purified by silica gel column chromatography, using an initial eluent of ethyl acetate, followed by an eluent of ethyl acetate/methanol (9:1). The appropriate fractions were combined and the solvent removed in vacuo, yielding the product as an off-white solid (85 mg, 68%). The product was isolated by trituration with diethyl ether, followed by drying, yielding the pure product as a fine white powder (55 mg, 44%).

$^1$H-nmr ($d_6$-DMSO;300 MHz):8.67 (1H, s, H-4), 6.43 (1H, s, H-5), 6.16 (1H,dd, $^3J$=6.0 Hz,H-1'), 5.29 (1H, d, $^3J$=4.1 Hz, 3'-OH), 5.13 (1H, m, 5'-OH), 4.22 (1H, m, H-3'), 3.89 (1H, m, H-4'), 3.63 (2H, m, H-5'), 2.64 (2H, t, α-$CH_2$), 2.35 and 2.06 (2H, m, H-2', and H-2'$_b$), 1.61 (2H, m, β-$CH_2$), 1.30 (4H, m, 2×$CH_3$), 0.87 (3H, m, $CH_3$). $^{13}$C-nmr ($d_6$-DMSO; 75 MHz): 14.1 ($CH_3$), 22.0, 26.3 (2×$CH_2$), 27.5 (β-$CH_2$), 30.8 (α-$CH_2$), 41.4 (C-2'), 60.9 (C-5'), 69.8 (C-3'), 87.6, 88.3 (C-1' and C-4'), 100.0 (C-5), 106.6 (C-4a), 137.0 (C-4), 154.0 (C-2), 158.5 (C-6), 171.4 (C-7a).

EXAMPLE 6

3-(2'-Deoxy-β-D-ribofuranosyl)-6-heptyl-2,3-dihydrofuro[2,3-d]pyrimidin-2-one

To a stirred solution of 5-iodo-2'-deoxyuridine (800 mg, 2.26 mmol) in dry dimethylformaldehyde (8 ml), at room temperature under a nitrogen atmosphere, was added dry diisopropylethylamine (584 mg, 0.80 ml, 4.52 mmol), 1-nonyne (842 mg, 1.11, 6.78 mmol), tetrakis (triphenylphosphine) palladium (O) 261 mg, 0.226 mmol) and copper (I) iodide (86 mg, 0.452 mmol). The reaction mixture was stirred at room temperature for 20 hours, after which time t.l.c. (ethyl acetate/methanol (95:9)) of the reaction mixture showed complete conversion of the starting material. Copper (I) iodide (80 mg, 0.40 mmol) and triethylamine (15 ml) and methanol (20 ml) were then added to the reaction mixture which was subsequently heated to reflux for 8 hours. The reaction mixture was then concentrated in vacuo and the resulting residue was dissolved in dichloromethane/methanol (1:3) (20 ml) and an excess of Amberlite IRA-400 ($HCO_3^-$ form) and solid sodium thiosulfate was added and the mixture was stirred for 30 minutes. The mixture was then filtered through silica which was subsequently washed with dichloromethane/methanol (6:4) and the combined filtrate was evaporated to dryness. The crude product was initially triturated with hexane and then purified by silica gel column chromatography using an initial eluent ethyl acetate, followed by an eluent of ethyl acetate/methanol (9:1). The appropriate fractions were combined and the solvent removed in vacuo to yield the product as a yellow solid (660 mg, 84%). Trituration of the product with dichloromethane yielded the pure product as a cream solid (484 mg, 61%).

$^1$H-nmr ($d_6$-DMSO;300 MHz):8.67 (1H,s,H-4), 6.43 (1H, s,H-5), 6.16 (1H, dd, $^3J$=5.3 Hz, 6.0 Hz, H-1'), 5.29 (1H, d, $^3J$=4.0 Hz, 3'-OH), 5.13 (1H, t, 5'-OH), 4.22 (1H, m, H-3'), 3.90 (1H, m, H-4'), 3.63 (2H, m, H-5'), 2.63 (2H, t, $^3J$=7.2 Hz, α-$CH_2$), 2.35 and 2.06 (2H, m, H-2'$_a$ and H-2'$_b$), 1.60 (2H, m, β-$CH_2$), 1.25 (8H, br.m, 4×$CH_2$) 0.85 (3H, m, $CH_3$). $^{13}$C-nmr ($d_6$-DMSO;75MHz): 16.3 ($CH_3$), 24.5, 28.8, 29.8, 30.8 (5×$CH_2$), 33.6 (α-$CH_2$), 43.6 (C-2'), 63.2 (C-5'), 72.1 (C-3'), 89.8, 90.5 (C-1' and C4'), 102.2 (C-5), 108.8 (CO4a), 139.2 (C-4), 156.2 (C-2), 160.7 (C-6), 173.6 (C-7a)

Each of the products of Examples 5 and 6 in which R is respectively C5 and C7 was tested in vitro in tissue culture assays for potent anti viral action with respect to Varicella zoster virus (VZV). The results in terms of $EC_{50}$ which was defined as the drug concentration (in $\mu M$) required to reduce virus-induced cytopathicity by 50% are given in Table II below. Equivalent figures for measurements on equivalent compounds embodying the present invention wherein R is C6, C8, C10 or C12, and for acyclovir are also given in the table.

TABLE II

| Compound: X = O | $EC_{50}$/VZV/$\mu M$ |
|-----------------|------------------------|
| R:              |                        |
| C5              | 3                      |
| C6              | 1.3                    |
| C7              | 0.17                   |
| C8              | 0.03                   |
| C10             | 0.005                  |
| C12             | ≦1.2                   |
| Acyclovir       | 0.2                    |

Each of the compounds embodying the present invention shows anti-viral activity greater than or comparable with acyclovir showing increasing efficacy along the series C5 to C10.

EXAMPLES 7, 8 AND 9

Examples 7, 8 and 9 demonstrate the preparation of compounds having a substituted R alkyl group and their efficacy as anti-viral agents. In each case the alkyl group is nC9 and the substituent is terminal. With respect to formula I above, in each case, X is O, Z is O, R' and R" are each H, Q is O, W is H, T is OH and T' and T''' is H.

EXAMPLE 7

3-(2'-Deoxy-β-D-ribofuranosyl)-6-(9-hydroxynonyl)-2,3'-dihydrofuro[2,3-d]pyrimidin-2-one To a stirred solution of 5-(11-hydroxy-1-undecynyl)-2'-deoxyuridine (200 mg, 0.51 mmol) in methanol/ triethylamine (7:3) (20 ml), at room temperature under a nitrogen atmosphere, was added copper (I) iodide (20 mg, 0.10 mmol). The reaction mixture was then heated to reflux and stirred for 4 hours. The solvent was removed in vacuo and the crude product purified by silica gel column chromatography, using an initial eluent of ethyl acetate, followed by an eluent of ethyl acetate/methanol (95:5). The appropriate fractions were combined and the solvent removed in vacuo, yielding the product (147 mg, 74%) as a pale yellow solid. The product was triturated with dichloromethane, followed by drying, yielding the pure product as a fine white powder suitable for biological testing and elemental analysis.

$^1$H-nmr (d$_6$-DMSO; 300 MHz): 8.67 (1H,s,H-4), 6.43. (1H,s,H-5), 6.16 (1H,dd,$^3$J=6.0 Hz,H-1'),5.28(1H,d,$^3$J=4.2 Hz,3'-OH), 5.12(1H,t,$^3$J=5.3 Hz,5'-OH),4.33(1H,t,$^3$J=4.9 Hz,5.3 Hz, alkyl-OH),4.22(1H,m,H-3'),3.90(1H,m,H-4'), 3.64(2H,m,H-5'),2.64 (2H,t,$^3$J=7.2 Hz,α-CH$_2$),2.35 and 2.04(2H,m,H-2'$_a$ and H2'$_b$), 1.61(2H,m,β-CH$_2$),1.39–1.25 (14H,m,7×CH$_2$). $^{13}$C-nmr(d$_6$-DMSO;75 MHz):27.2,28.1, 29.1,30.1,30.4,30.7(×2),34.3(8×CH$_2$),42.9 (C-2'),62.4,62.5 (C-5',CH$_2$CH$_2$OH),71.4(C-3'),89.1,89.8(C-1' and C-4'), 101.5(C-5),108.1(C-4a),138.5(C-4),155.5 (C-2),160.1(C-6), 172.9(C-7a). Mass spectrum (ES–MS(+ve)); m/z 433(20%, [M+K]$^+$),417(100%,[M+Na]$^+$),395(20%, [M+H]$^+$), 279 (100%, [base+H]$^+$).

EXAMPLE 8

6-(9-chlorononyl)-3-(4-hydroxy-5-(hydroxymethyl) tetrahydro -2-furanyl)-2,3-dihydrofuro[2,3,-d] pyrimidin-2-one To a stirred solution of crude 5-(11-chloro-1-undecynyl)- 1-(4-hydroxy-5-hydroxymethyl)tetrahydro-2-furanyl)1,2,3, 4-tetrahydro-2,4,-pyrimidinedione (280 mg) in methanol/ triethylamine (7:3) (20 ml), at room temperature under a nitrogen atmosphere, was added copper(I)iodide (15.2 mg, 0.08 mmol). The reaction mixture was then heated to reflux and stirred for 5 hours. The solvent was removed in vacuo and the crude product purified twice by silica gel column chromatography, using ethyl acetate/methanol (9:1) as the eluent. The appropriate fractions were combined and the solvent removed in vacuo, yielding a yellow solid, the crude product (230 mg, 71%). The crude product was then triturated and crystallised with acetone and dried to yield the pure product as a fine white solid.

1H-NMR (d6-DMSO; 300 MHz): 8.67(1H,s,H-4), 642 (1H,s,H-4), 642 (1H,s,H-5),6.16 (1H,t,3J=6.0 Hz, H-1'), 5.28 (1H,d,3J=4.2 Hz,3'-OH), 5.12 (1H,t,3J=5.1 Hz, 5'-OH), 4.21 (1H,m,H-3'), 3.94 (1H,m,H-4'), 3.56(4H,m,H-5' and CH2Cl), 2.64 (2H,t,3J=7.2 Hz,a-CH2), 2.34, 2.05 (2H,m,H-2'a and H-2'b), 1.75 (2H,m,b-CH2), 1.61, 1.44, 1.25 (12H, m,6×CH2).

13C-NMR (d6-DMSO;75 MHz): 172.0 (C-7a), 159.1 (C-6), 154.6 (C-2), 137.6 (C-4), 107.2 (C-4a), 100.6 (C-5), 88.9, 88.2 (C-1' and C-4'), 70.5 (C-3'), 61.6 (C-5'), 46.2 (CH2Cl), 42.0 (C-2'), 30.0, 29.6, 29.4, 29.2, 29.2, 28.2, 27.4 26.5, (8×CH2).

Mass Spectrum (ES–MS(+ve)):m/z 450 (20%[M+K]+), 435 (45%[M+Na]+), 412 (30%[M+H]+), 297 (10%[Base+ H]+).

Each of the products of Examples 7 and 8 was tested in vitro in tissue culture assays for potent antiviral action with respect to varicella zoster virus (VZV). Acyclovir was included in the test procedure as a control. EC$_{50}$ and CC$_{50}$ values were measured as described under examples 1 to 6 above.

The results are given in Table III below.

TABLE III

| Example | R | EC$_{50}$/VZV/μM | CC$_{50}$/μM |
|---------|---|------------------|--------------|
| 7 | —C$_9$H$_{18}$OH | 0.4 | >200 |
| 8 | —C$_9$H$_{18}$Cl | 0.006 | >200 |
| Acyclovir | | 0.2 | >100 |

The product of Example 8 was additionally tested in vitro in tissue culture assays for potent antiviral action with respect to cytomegalovirus (CMV). CMV induced cytopatho-genicity in human embryonic lung fibroblast (HEL) cells was measured post infection. EC$_{50}$ and CC$_{50}$ were defined as above for VZV. The equivalent data for the known CMV active agent dihydroxypropyl guanine (DHPG) is included in Table IV as a control. The results are given in Table IV below.

TABLE IV

| Example | R | EC$_{50}$/CMV/μM | CC$_{50}$/μM |
|---------|---|------------------|--------------|
| 8 | —C$_9$H$_{18}$Cl | 7.2 | 200 |
| DHPG | | 3.1 | >200 |

The product of Example 8 with R equal to —C$_9$H$_{18}$Cl shows antiviral activity with respect to CMV comparable to DHPG.

EXAMPLES 9 AND 10

Examples 9 and 10 are both comparative Examples. They are each equivalent to the compounds of Examples 1 to 8 with the exception that the R group is respectively —C$_3$H$_6$OH and —C$_4$H$_8$OH.

EXAMPLE 9

3-(2'-Deoxy-β-D-ribofuranosyl)-6-(3-hydroxypropyl)-2,3-dihydrofuro[2,3-d]pyrimidin-2-one To a stirred solution of 5-(5-hydroxy-1-pentynyl)-2'-deoxyuridine (200 mg, 0.64 mmol) in methanol/ triethylamine (7:3) (20 ml), at room temperature under a nitrogen atmosphere, was added copper (I) iodide (20 mg, 0.10 mmol). The reaction mixture was then heated to reflux and stirred for 4 hours. The solvent was removed in vacuo and the crude product purified by silica gel column chromatography, using an initial eluent of ethyl acetate, changing to an eluent of ethyl acetate/methanol (7:3) via a gradient. The appropriate fractions were combined and the solvent removed in vacuo, yielding the product (102 mg, 51%) as a pale yellow solid. The product was purified further by recrystallization from ethanol.

$^1$H-nmr (d$_6$-DMSO; 300 MHz): 8.67 (1H,s,H-4), 6.44 (1H,s,H-5), 6.16 (1H,dd,$^3$J=6.0 Hz,H-1'), 5.29 (1H,d,$^3$J=4.2 Hz, 3'-OH), 5.13 (1H,m,5'-OH), 4.59 (1H,m,alkyl-OH), 4.21 (1H,m,H-3'), 3.90 (1H, m,H-4'), 3.64 (2H,m,H-5'), 3.45 (2H,m,CH$_2$CH$_2$OH), 2.69 (2H,m,α-CH$_2$), 2.35 and 2.06 (2H,m,H-2'$_a$ and H-2'$_b$), 1.75 (2H,m,CH$_2$). $^{13}$C-nmr (d$_6$-DMSO; 75 MHz): 25.0 (CH$_2$CH$_2$OH), 42.0 (C-2'), 60.5, 61.6 (C-5',CH$_2$CH$_2$OH), 70.5 (C-3'), 88.2, 88.9 (C-1' and C-4'), 100.5 (C-5), 107.2 (C-4a), 137.6 (C-4), 154.6 (C-2), 159.1 (C-6), 172.0 (C-7a). Mass spectrum (ES–MS (+ve)); m/z 374 (15%, [M+Cu]$^+$), 349 (10%, [M+K]$^+$), 333 (25%, [M+Na]$^+$) , 311 (20%, [M+H]$^+$), 195 (100%, [base+H]$^+$) .

Elemental analysis (found: C, 54.23%; H, 5.98%; N,8.84:. $C_{14}H_{18}N_2O_6$ requires: C, 54.19%; H, 5.8%; N, 9.03%).

EXAMPLE 10

3-(2'-Deoxy-β-D-ribofuranosyl)-6-(4-hydroxybutyl)-2,3-dihydrofuro[2,3-d]pyrimidin-2-one To a stirred solution of 5-(6-hydroxy-1-hexynyl)-2'-deoxyuridine (300 mg, 0.92 mmol) in methanol/triethylamine (7:3) (20 ml), at room temperature under a nitrogen atmosphere, was added copper (I) iodide (20 mg, 0.10 mmol). The reaction mixture was then heated to reflux and stirred for 3 hours. The solvent was removed in vacuo and the crude product purified by silica gel column chromatography, using an initial eluent of ethyl acetate, changing to an eluent of ethyl acetate/methanol (8:2) via a gradient. The appropriate fractions were combined and the solvent removed in vacuo, yielding the product (162 mg, 54%) as a pale yellow solid. The product was purified further by recrystallization from ethanol.

$^1$H-nmr (d$_6$-DMSO; 300 MHz): 8.67 (1H,s,H-4), 6.43 (1H,s,H-5), 6.16 (1H,dd,$^3$J=6.0 Hz,H-1'), 5.29 (1H,d,$^3$J=4.1 Hz, 3'-OH), 5.14 (1H,t,$^3$J=5 Hz, 5'-OH), 4.44 (1H,t,$^3$J=5 Hz, alkyl-OH), 4.21 (1H,m,H-3'), 3.90 (1H,m,H-4'), 3.63 (2H, m,H-5'), 3.41 (2H,m,CH$_2$CH$_2$OH), 2.65 (2H,t,$^3$J=7.2 Hz, α-CH$_2$), 2.35 and 2.04 (2H,m,H-2'$_a$ and H-2'$_b$), 1.64 and 1.46 (4H,m,2×CH$_2$). $^{13}$C-nmr (d$_6$-DMSO; 75 MHz): 23.3, 27.4 (2×CH$_2$), 31.9 (α-CH$_2$), 41.4 (C-2'), 60.4, 61.0 (C-5', CH$_2$CH$_2$OH), 69.9 (C-3'), 87.6, 88.3 (C-1' and C-4'). 100.0 (C-5), 106.6 (C-4a), 137.0 (C-4), 153.5 (C-2), 158.5 (C-6), 171.4 (C-7a). Mass spectrum (ES–MS(+ve)); m/z 388 (10%, [M+Cu]$^+$), 363 (10%,[M+K]$^+$), 347 (20%,[M+Na]$^+$), 325 (20%, [M+H]$^+$), 209 (100%, [base+H]$^+$). Elemental analysis (found: C,55.34%; H, 6.41%; N, 8.84%. $C_{15}H_{20}N_2O_6$ requires: C,55.55%; H, 6.22%; N, 8.64%).

The products of Example 9 and 10 were each tested in vitro in tissue culture assays for potent anti viral action with respect to Varicella zoster virus (VZV). The values of EC$_{50}$ and CC$_{50}$ were measured as above. The results are given in Table V below and include those for acyclovir as control.

TABLE V

| Example | R | EC$_{50}$/VZV/μM | CC$_{50}$/μM |
|---|---|---|---|
| 9 | —C$_3$H$_6$OH | 9.7 | >200 |
| 10 | —C$_4$H$_8$OH | 29 | >200 |
| Acyclovir |  | 0.2 | >100 |

Neither the product of Example 9 nor the product of Example 10 demonstrated useful VZV antiviral activity having regard to the control. The low activity is attributed to the short alkyl chain length.

EXAMPLE 11

The present example investigated the effect of altering Q in the above general formula to sulphur.

The compound prepared in terms of the above formula had R=—C$_9$H$_{19}$, X=O, R'=R"=H, Q=S, Z=O, W=H, T=OH and T'=T"=H.

The compound was prepared by reactions analogous to Example 2, using 4'-thio nucleoside.

The compound was assessed by in vitro tissue culture assay for potent antiviral action with respect to varicella zoster virus (VZV) as described above. The results are given in Table VI below.

TABLE VI

| Example | R | T | T' | T" | Q | EC$_{50}$/VZV/μM | CC$_{50}$/μM |
|---|---|---|---|---|---|---|---|
| 11 | —C$_9$H$_{19}$ | OH | H | H | S | 0.006 | 93 |

The product of example 16 shows extremely potent antiviral activity with respect to varicella zoster virus.

EXAMPLES 12 TO 15

Each of Examples 12 to 15 describes compounds according to the above general formula wherein X is NH.

In Examples 12 to 15 in accordance with the above general formula Z=O, Q=O, W=H, T=OH, T'=T"=H, R'=R"=H and R is respectively —C$_6$H$_{11}$, —C$_8$H$_{17}$ and —C$_{12}$H$_{25}$.

EXAMPLE 12

3-(2'-Deoxy-β-D-ribofuranosyl)-6-hexyl,3,7-dihydro-2H-pyrrolo[2,3-d]pyrimidin-2-one To a solution of 3-(2'-Deoxy-β-D-ribofuranosyl)-6-hexyl-2,3-dihydrofuro[2,3-d]pyrimidin-2-one in methanol (5 ml) was added 33% aqueous ammonia (5 ml). The reaction vessel was sealed and the reaction mixture heated at ca 50° C. for 20 hours. The solvent was removed in vacuo and the crude product was purified by column chromatography using an eluent of dichloromethane/methanol (9:1). The appropriate fractions were combined and the solvent removed in vacuo to give the pure product as a glassy solid (48 mg, 60%). The product was then collected as a white powder by trituration with diethyl ether.

$^1$H-nmr (d$_6$-DMSO;300 MHz): 11.04 (1H,s,NH-7, 8.48 (1H,s, H-4), 6.24 (1H, dd, $^3$J=6.4 Hz,H-1'), 5.90 (1H, s, H-5, 5.25 (1H, d, $^3$J=4.1 Hz, 3'-OH), 5.10 (1H, t, 5'-OH), 4.22 (1H, m, H-3'), 3.86 (1H, m, H-4'), 3.63 (2H, m, H-5'), 2.28 and 1.99 (2H, m, H-2'$_a$ and H-2'$_b$), 1.59 (2H, m, α-CH$_2$), 1.27 (8H, br.m, 4×CH$_2$), 0.85 (3H, t, CH$_3$). $^{13}$C-nmr (d$_6$-DMSO: 75 MHz) 14.7 (CH$_3$), 22.8, 2×28.3, 29.0 (4×CH$_2$), 31.8 (α-CH$_2$), 42.1 (C-2'), 61.8 (C-5'), 70.7 (C-3'), 87.4, 88.5 (C-1' and C-4'), 97.0 (C-5), 109.6 (C-4a), 135.2 (C-4), 143.2 (C-6), 154.6 (C-2); peak for 7a too small to identify.

EXAMPLE 13

3-(2'-Deoxy-β-D-ribofuranosyl)-6-octyl,3,7-dihydro-2H-pyrrolo[2,3-d]pyrimidin-2-one To a solution of 3-(2'-Deoxy-β-D-ribofuranosyl)-6-octyl-2,3-dihydrofuro[2,3-d]pyrimidin-2-one in methanol (5 ml) was added 33% aqueous ammonia (5 ml). The reaction vessel was sealed and the reaction mixture heated at ca. 50° C. for 20 hours. The solvent was removed in vacuo and the crude product was purified by column chromatography using an eluent of dichloromethane/methanol (9:1). The appropriate fractions were combined and the solvent removed in vacuo and the product (79 mg, 79%) isolated as a cream powder by trituration with diethyl ether.

$^1$H-nmr (d$_6$-DMSO;300 MHz): 11.13 (1H,s, NH-7), 8.51 (1H, s, H-4), 6.26 (1H, dd, $^3$J=6.4 Hz, H-1'), 5.91 (1H, s, H-5), 5.29 (1H, m, 3'-OH), 5.14 (1H, m, 5'-OH), 4.24 (1H, m, H-3'), 3.88 (1H, m, H-4'), 3.65 (2H,m,H-5'), 2.30 and 2.00 (2H,m, H-2'$_a$ and H-2'$_b$), 1.60 (2H, m, α-CH$_2$), 1.24 (12H, br.m, 6×CH$_2$), 0.85 (3H, m, CH$_3$). $^{13}$C-nmr (d$_6$-DMSO; 75 MHz: 16.5 (CH$_3$), 24.6, 30.0 30.1, 31.0, 31.1, 13.2, (6×CH$_2$), 33.8 (α-CH$_2$), 43.9 (C-2'), 63.5 (C-5'), 72.4

(C-3'), 89.2, 90.2 (C-1' and C-4'), 98.8 (C-5), 111.3 (C-4a), 136.9 (C-4), 144.9 (C-6), 156.4 (C-2); 161.7 (C-7a).

EXAMPLE 14

3-(2'-Deoxy-β-D-ribofuranosyl)-6-dodecyl-3,7-dihydro-2H-pyrollo[2,3-d]pyrimidin-2-one The above compound was prepared by a method analogous to that described under Examples 12 and 13 above.

EXAMPLE 15

In a compound wherein X is N—H the effect of varying Q to S was investigated. With respect to the above general formula other components were R=—$C_8H_{19}$, R'=R"=H, W=H, T=OH, Z=O and T'=T"=H.

The compound was prepared by reactions analogous to Example 13 using 4' thionucleoside.

Each of the products of examples 12 to 15 was tested in vitro in tissue culture assays for potent antiviral action with respect to varicella zoster virus (VZV) as described above under Examples 1 to 4. The results are given in Table VII below.

TABLE VII

| Example | R | X | Q | $EC_{50}$/VZV/$\mu$M | $CC_{50}$/$\mu$M |
|---|---|---|---|---|---|
| 12 | —$C_6H_{15}$ | —NH | O | >50 | |
| 13 | —$C_8H_{15}$ | —NH | O | 0.15 | |
| 14 | —$C_{12}H_{25}$ | —NH | O | 3.7 | >200 |
| 15 | —$C_9H_{19}$ | —NH | S | 0.21 | 200 |

Each of the products of Examples 13 to 15 displayed antiviral effect with respect to varicella zoster virus.

What is claimed is:

1. A compound having the formula:

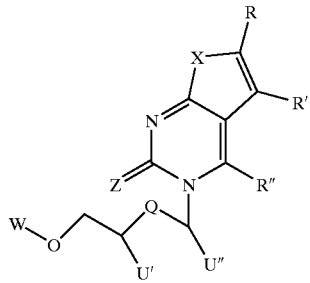

wherein:
R is selected from the group consisting of $C_6$ to $C_{20}$ alkyl, $C_5$ to $C_{20}$ cycloalkyl, halogens, aryl and alkylaryl, with the proviso that R is not 4-$FC_6H_4$, $C_6F_5$, 4-$MeOC_6H_4$, 3,5-$(CF_3)_2C_6H_3$, 3,5-$F_2C_6H_3$, 4$CF_3C_6H_4$, or $C_6H_5$;
R' is selected from the group consisting of hydrogen, alkyl, cycloalkyl, halogens, amino, alkylamino, dialkylamino, nitro, cyano, alkyoxy, aryloxy, thiol, alkylthiol, arythiol, and aryl;
R" is selected from the group consisting of hydrogen, alkyl, cycloalkyl, halogens, alkyloxy, aryloxy, and aryl;
Q is selected from the group consisting of O, S, and $CY_2$, where Y may be the same or different and is selected from the group consisting of H, alkyl, and halogens;
X is selected from the group consisting of O, NH, S, N-alkyl, $(CH_2)_n$ where n is 1 to 10, and $CY_2$, where Y may be the same or different and is selected from H, alkyl, and halogens, with the proviso that when R is an unsubstituted $C_6$ to $C_{10}$ alkyl group and Q is O, X is other than NH or N-alkyl;
Z is selected from the group consisting of O, S, NH, and N-alkyl;
U' and U" are joined so as to form a ring moiety wherein U'—U" together is respectively selected from the group consisting of —CTH—CT'T"— and —CT=CT—, and —CT'=CT'—, so as to provide ring moieties selected from the group consisting of:

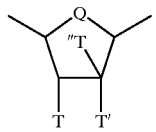 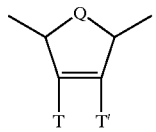

wherein:
T is selected from the group consisting of OH, H, halogens, O-alkyl, O-acyl, O-aryl, CN, $NH_2$, and $N_3$;
T' is selected from the group consisting of H and halogens and where more than one T' is present they may be the same or different;
T" is selected from the group consisting of H and halogens; and
W is selected from the group consisting of H, a phosphate group, and a pharmacologically acceptable salt or prodrug thereof.

2. The compound of claim 1 wherein R is a $C_7$ to $C_{20}$ alkyl group.

3. The compound of claim 2 wherein R is a $C_8$ to $C_{14}$ alkyl group.

4. The compound of claim 1 wherein R' and R" are each H.

5. The compound of claim 1 wherein Q is O.

6. The compound of claim 1 wherein X is O.

7. The compound of claim 1 wherein Z is O.

8. The compound of claim 1 wherein U' and U" are joined to provide the saturated ring moiety

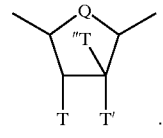

9. The compound of claim 1 wherein T is OH.

10. The compound of claim 1 wherein each of T' and T" is H.

11. A method for preparing a compound according to claim 1 comprising either:
    (a) contacting a 5-halo nucleoside analog with a terminal alkyne in the presence of a copper catalyst, or
    (b) cyclizing a 5-alkynyl nucleoside in the presence of a copper catalyst.

12. A method of prophylaxis or treatment of a viral infection, wherein the virus is selected from the group consisting of varicella zoster virus and cytomegalovirus, comprising administration to a patient in need of such treatment an effective dose of a compound having the formula:

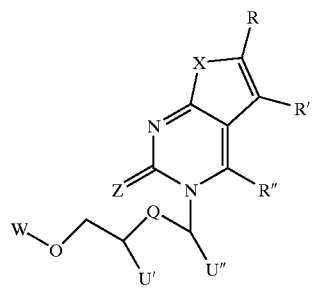

wherein:

R is selected from the group consisting of $C_6$ to $C_{20}$ alkyl, $C_5$ to $C_{20}$ cycloalkyl, halogens, aryl and alkylaryl, R' is selected from the group consisting of hydrogen, alkyl, cycloalkyl, halogens, amino, alkylamino, dialkylamino, nitro, cyano, alkyoxy, aryloxy, thiol, alkylthiol, arythiol, and aryl;

R" is selected from the group consisting of hydrogen, alkyl, cycloalkyl, halogens, alkyloxy, aryloxy, and aryl;

Q is selected from the group consisting of O, S, and $CY_2$, where Y may be the same or different and is selected from the group consisting of H, alkyl, and halogens;

X is selected from the group consisting of O, NH, S, N-alkyl, $(CH_2)_n$ where n is 1 to 10, and $CY_2$, where Y may be the same or different and is selected from H, alkyl, and halogens, with the proviso that when R is an unsubstituted $C_6$ to $C_{10}$ alkyl group and Q is O, X is other than NH or N-alkyl;

Z is selected from the group consisting of O, S, NH, and N-alkyl;

U' and U" are joined so as to form a ring moiety wherein U'—U" together is respectively selected from the group consisting of —CTH—CT'T"— and —CT=CT—, and —CT'=CT'—, so as to provide ring moieties selected from the group consisting of:

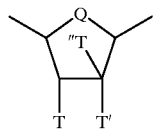

wherein:

T is selected from the group consisting of OH, H, halogens, O-alkyl, O-acyl, O-aryl, CN, $NH_2$, and $N_3$;

T' is selected from the group consisting of H and halogens and where more than one T' is present they may be the same or different;

T" is selected from the group consisting of H and halogens; and

W is selected from the group consisting of H, a phosphate group, and a pharmacologically acceptable salt or prodrug thereof.

13. A pharmaceutical composition comprising a compound having the formula:

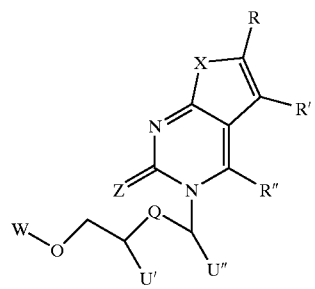

wherein:

R is selected from the group consisting of $C_6$ to $C_{20}$ alkyl, $C_5$ to $C_{20}$ cycloalkyl, halogens, aryl and alkylaryl, with the proviso that R is not $4-FC_6H_4$, $C_6F_5$, $4-MeOC_6H_4$, $3,5-(CF_3)_2C_6H_3$, $3,5-F_2C_6H_3$, $4-CF_3C_6H_4$, or $C_6H_5$;

R' is selected from the group consisting of hydrogen, alkyl, cycloalkyl, halogens, amino, alkylamino, dialkylamino, nitro, cyano, alkyoxy, aryloxy, thiol, alkylthiol, arythiol, and aryl;

R" is selected from the group consisting of hydrogen, alkyl, cycloalkyl, halogens, alkyloxy, aryloxy, and aryl;

Q is selected from the group consisting of O, S, and $CY_2$, where Y may be the same or different and is selected from the group consisting of H, alkyl, and halogens;

X is selected from the group consisting of O, NH, S, N-alkyl, $(CH_2)_n$ where n is 1 to 10, and $CY_2$, where Y may be the same or different and is selected from H, alkyl, and halogens, with the proviso that when R is an unsubstituted $C_6$ to $C_{10}$ alkyl group and Q is O, X is other than NH or N-alkyl;

Z is selected from the group consisting of O, S, NH, and N-alkyl;

U' and U" are joined so as to form a ring moiety wherein U'—U" together is respectively selected from the group consisting of —CTH—CT'T"— and —CT=CT—, and —CT'=CT'—, so as to provide ring moieties selected from the group consisting of:

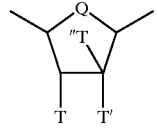 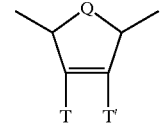

wherein:

T is selected from the group consisting of OH, H, halogens, O-alkyl, O-acyl, O-aryl, CN, $NH_2$, and $N_3$;

T' is selected from the group consisting of H and halogens and where more than one T' is present they may be the same or different;

T" is selected from the group consisting of H and halogens; and

W is selected from the group consisting of H, a phosphate group, and a pharmacologically acceptable salt or prodrug thereof;

and a pharmaceutically acceptable excipient.

14. A method of preparing a pharmaceutical composition comprising the step of combining a compound having the formula:

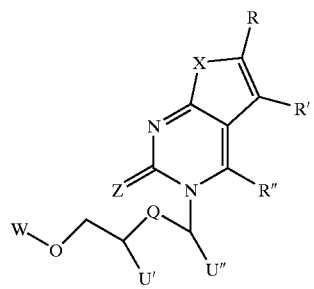

wherein:

R is selected from the group consisting of $C_6$ to $C_{20}$ alkyl, $C_5$ to $C_{20}$ cycloalkyl, halogens, aryl and alkylaryl, with the proviso that R is not $4\text{-}FC_6H_4$, $C_6F_5$, $4\text{-}MeOC_6H_4$, $3,5\text{-}(CF_3)_2C_6H_3$, $3,5\text{-}F_2C_6H_3$, $4\text{-}CF_3C_6H_4$, or $C_6H_5$;

R' is selected from the group consisting of hydrogen, alkyl, cycloalkyl, halogens, amino, alkylamino, dialkylamino, nitro, cyano, alkyoxy, aryloxy, thiol, alkylthiol, arythiol, and aryl;

R" s selected from the group consisting of hydrogen, alkyl, cycloalkyl, halogens, alkyloxy, aryloxy and aryl;

Q is selected from the group consisting of O, S, and $CY_2$, where Y may be the same or different and is selected from the group consisting of H, alkyl, and halogens;

X is selected from the group consisting of O, NH, S, N-alkyl, $(CH_2)_n$ where n is 1 to 10, and $CY_2$, where Y may be the same or different and is selected from H, alkyl, and halogens, with the proviso that when R is an unsubstituted $C_6$ to $C_{10}$ alkyl group and Q is O, X is other than NH or N-alkyl;

Z is selected from the group consisting of O, S, NH, and N-alkyl;

U' and U" are joined so as to form a ring moiety selected from the group consisting of —CTH—CT'T"— and —CT=CT—, and —CT'=CT'—, so as to provide ring moieties selected from the group consisting of:

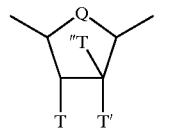 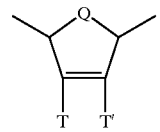

wherein:

T is selected from the group consisting of OH, H, halogens, O-alkyl, O-acyl, O-aryl, CN, $NH_2$, and $N_3$;

T' is selected from the group consisting of H and halogens and where more than one T' is present they may be the same or different;

T" is selected from the group consisting of H and halogens; and

W is selected from the group consisting of H, a phosphate group, and a pharmacologically acceptable salt or prodrug thereof;

with a pharmaceutically acceptable excipient.

* * * * *